United States Patent [19]

Motomura et al.

[11] Patent Number: 5,739,540
[45] Date of Patent: Apr. 14, 1998

[54] NUCLEAR MEDICINE DIAGNOSTIC APPARATUS

[75] Inventors: Nobutoku Motomura, Tochigi-ken; Takashi Ichihara, Otawara; Hiroharu Kawahara, Kuroiso, all of Japan

[73] Assignee: Kabushiki Kaisha Toshiba, Kawasaki, Japan

[21] Appl. No.: 668,230

[22] Filed: Jun. 21, 1996

[30] Foreign Application Priority Data

Jun. 23, 1995 [JP] Japan .................................. 7-157266

[51] Int. Cl.⁶ .............................. G21K 5/00; G21K 5/02
[52] U.S. Cl. .............................. 250/363.04; 250/493.1; 250/494.1
[58] Field of Search ........................ 250/494.1, 493.1, 250/363.04, 363.05

[56] References Cited

U.S. PATENT DOCUMENTS

| | | |
|---|---|---|
| 5,055,687 | 10/1991 | Ichihara . |
| 5,210,421 | 5/1993 | Gullberg et al. .................. 250/363.04 |
| 5,227,968 | 7/1993 | Ichihara . |
| 5,296,708 | 3/1994 | Moyers et al. .................. 250/363.04 X |
| 5,371,672 | 12/1994 | Motomura et al. . |
| 5,471,061 | 11/1995 | Moyers et al. .................. 250/363.04 X |
| 5,650,625 | 7/1997 | Stoub .................. 250/494.1 X |

FOREIGN PATENT DOCUMENTS 58-92974  6/1983  Japan ................................ 250/363.04

OTHER PUBLICATIONS

Larsson et al., "Simultaneous SPECT and CT with Shutter Controlled Radionuclide Sources and Parallel Collimator Geometry," IEEE Transactions on Nuc. Sci., vol. 40, No. 4, Aug. 1993, pp. 1117–1122.

Tan et al., "A Scanning Line Source for Simuitaneous Emission and Transmission Measurements in SPECT," Journal of Nuclear Medicine, vol. 34, No. 10, Oct. 1993, pp. 1752–1760.

*Primary Examiner*—Edward J. Glick
*Attorney, Agent, or Firm*—Oblon, Spivak, McClelland, Maier & Neustadt, P.C.

[57] ABSTRACT

A nuclear medicine diagnostic apparatus, particularly involving emission computed tomography, wherein absorption correction is performed by a gamma ray source including a plurality of line sources arrayed in a common plane. Each line source produces a radiation distribution having a peak and defining a half-width distance at which the radiation from the line source is attenuated by one-half. The plurality of line sources are arranged at a pitch equal to the half-width distance or an integral multiple of the half-width distance. In one embodiment, a serpentine line source is used having straight line portions and a plurality of bent portions, with the straight line portions arrayed parallel to each other at a pitch equal to the half-width distance or an integral multiple of the half-width distance.

24 Claims, 7 Drawing Sheets

NUCLEAR MEDICINE DIAGNOSTIC APPARATUS

BACKGROUND OF THE INVENTION

1. Field of the Invention

The present invention relates to a nuclear medicine diagnostic apparatus.

2. Description of the Related Art

Medicines labeled with a radioisotope (RI) are gathered in a specific internal organ, which is fixed by a property of the medicines. Therefore, an RI-distribution in vivo is useful for diagnosis of a nidus or that of metabolism.

A Gamma camera counts gamma-rays emitted from RI of a subject (examining object) at a plurality of positions of the outside of the subject, thereby obtaining the RI-distribution in vivo.

An emission computed tomograph (ECT) counts the gamma-rays emitted from RI of the subject in a plurality of directions, so that a tomographic image is reconstructed on the number of counts.

In ECT, there is needed the so-called absorption correction in order to equalize variations of the number of counts, which are caused by a difference in the absorption rate of gamma rays. In order to correct the absorption, a distribution of absorption coefficient of the reconstruction cross section, that is, the so-called absorption coefficient map is needed. Similar to an X-ray CT, gamma-rays, which are emitted from a gamma ray source and transmitted through the subject, are detected in the plurality of directions to be counted, thereby reconstructing the absorption coefficient map.

Figure 1:
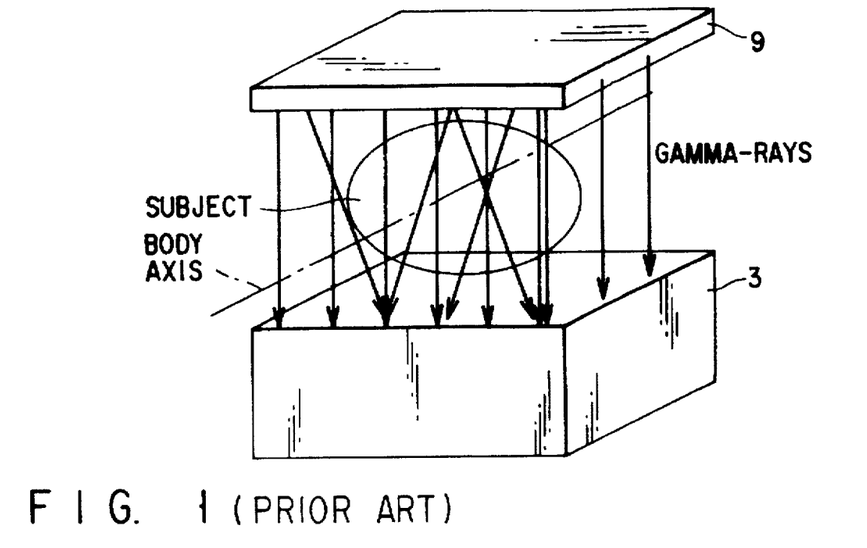
FIG. 1 is a view showing a conventional plane source.
Figure 3:
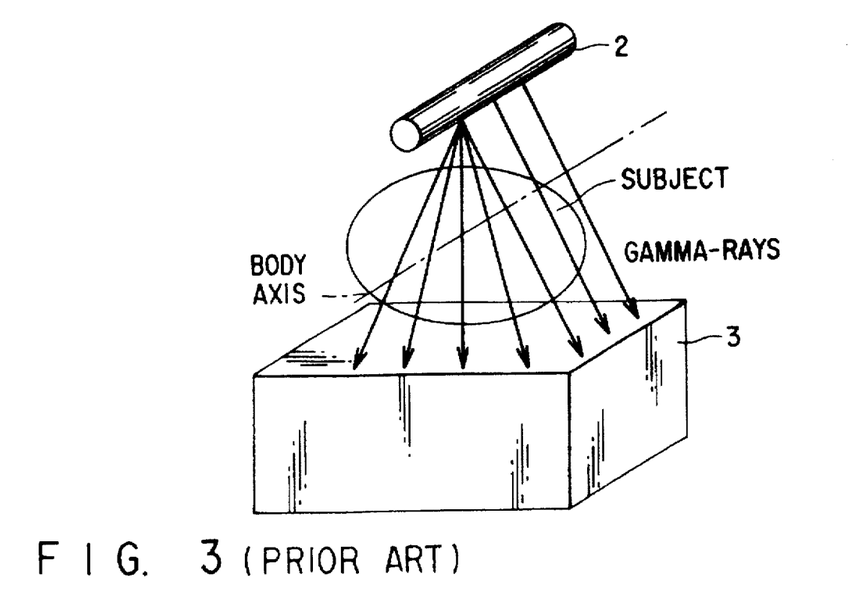
FIG. 3 is a cross sectional view of the plane source of FIG. 1.

As shown in FIGS. 1 and 3, a plane source 9 or a line source 2 is used as a source of radiation for an absorption correction. The line source 2 is provided to be parallel to a body axis of the subject.

In the use of the plane source 9, there is a problem in that an amount of a scattering component, which is made incident from a direction inclined to a detector 3. The use of a collimator for limiting the incident direction lightens the problem, but does not solve the problem. This problem causes the reduction of resolution.

Also, in the use of the plane source 9, the following problems are present.

Figure 2:
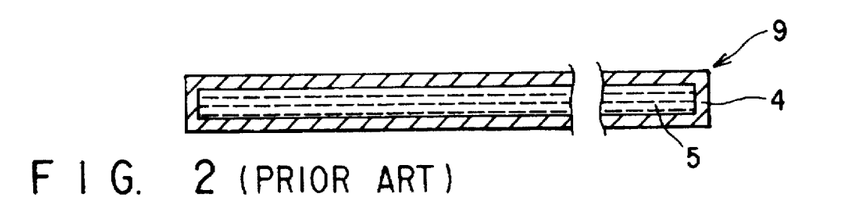
FIG. 2 is a view showing a conventional line source.

More specifically, FIG. 2 is a cross section of the plane source 9. The plane source 9 is structured such that a plate-like closed container 4 is filled with RI-solution. The plane source 9 is required to have a size enough to cover at least a diagnostic portion of the subject. Therefore, the closed container 4 is required to have strength enough not to be deformed by weight of RI solution. Due to this, the closed container 4 is formed of metal or glass. Then, there are problems in that the size of the plane source 9 is enlarged, or the weight is increased. Moreover, there is difficulty in that the closed container 4 is processed to be completely flat.

The above problems can be solved by the use of the line source 2. However, as shown in FIG. 2, since a radiation range of the gamma rays is narrow, the line source 2 is not suitable for an absorption correction of a cross section of the subject.

SUMMARY OF THE INVENTION

An object of the present invention is to provide a nuclear medicine diagnostic apparatus, which can suitably execute an absorption correction of a vertical cross section of a body axis of a subject.

According to the first aspect of the present invention, there is provided to a nuclear medicine diagnostic apparatus including a source of gamma-rays for an absorption correction, wherein the source has an array structure for a plurality of line sources.

According to the second aspect of the present invention, there is provided to a nuclear medicine diagnostic apparatus including a source of gamma-rays for an absorption Correction, wherein the source is structured such that one line source is provided in a plane form.

According to the third aspect of the present invention, there is provided to a nuclear medicine diagnostic apparatus including a source of gamma-rays for an absorption correction, wherein the source has a circulation path provided in a plane form and a point-source communicating with the circulation path.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

DETAILED DESCRIPTION OF THE PREFERRED EMBODIMENT

The following will explain the preferred embodiments of the nuclear medicine diagnostic apparatus of the present invention with reference to the drawings.

The nuclear medicine diagnostic apparatus can be roughly classified into a gamma camera for generating a plane-image, and an ECT (emission computed tomography) for reconstructing a tomogram. Also, the ECT can be classified into a SPECT (single photon emission computed tomography) and a PET (position emission computed tomography). The present invention can be applied to any of these nuclear medicine diagnostic apparatus. The ECT type nuclear medicine diagnostic apparatus is suitably used in the present invention. In this case, the following will explain SPECT.

Figure 4:
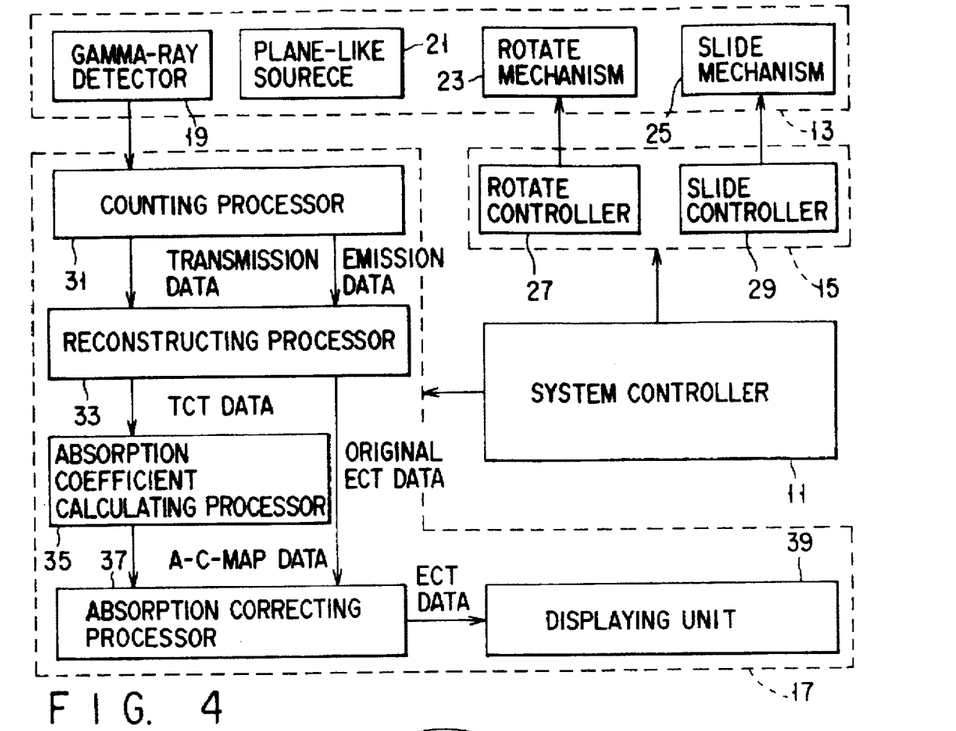
FIG. 4 is a block diagram of a nuclear medicine diagnostic apparatus of an embodiment of the present invention.
Figure 5:
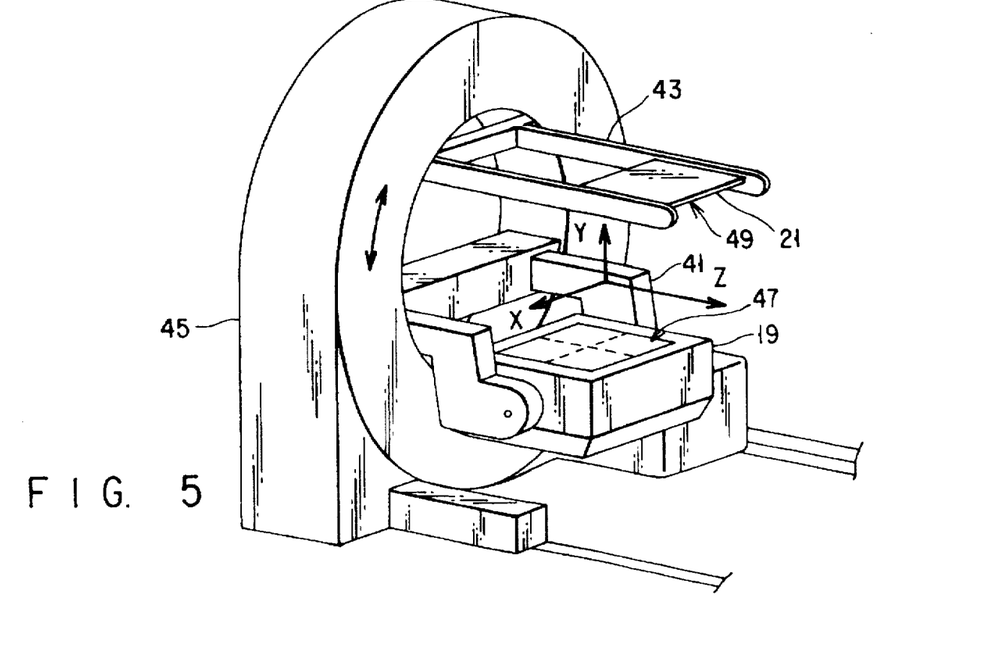
FIG. 5 is an outline view of a gantry of FIG. 4.

FIG. 4 shows the structure of the nuclear medicine diagnostic apparatus of the embodiment of the present invention. FIG. 5 shows an outline of a gantry. The nuclear medicine diagnostic apparatus of the embodiment of the present invention comprises a system controller 11, severing as a control center of the entire system, a gantry 13, a scan controller 15, and a processor unit 17.

The gantry 13 has a gamma-ray detector 19, a plane-like source 21, a rotate mechanism 23, and a slide mechanism 25. The gamma-ray detector 19 and the plane-like source 21 are supported by a stand 45 through arms 41 and 43 in a state that the detector 19 and the source 21 are opposite to each other to sandwich the subject therebetween.

Figure 6:
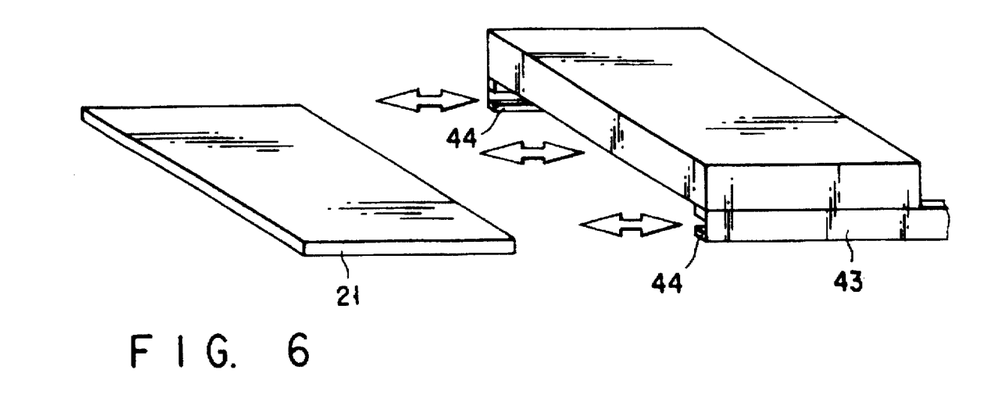
FIG. 6 is a perspective view of an arm of a plane-like source of FIG. 4.

As shown in FIG. 6, rails 44 are provided to the arm 43 to detach the plane-like source 21, if necessary. As an arm 43, relatively light acrylic is used.

The gamma-ray detector 19 is structured to detect the gamma-ray, which is substantially vertically made incident onto a detection surface 47, so as to output a signal corresponding to the incident position and energy. For example, the gamma-ray detector 19 comprises the structure having a scintillator and a plurality of photomultiplier tubes arrayed on the back surface of the scintillator, or a two-dimensional array structure of a semiconductor element. The gamma-rays, which are emitted from the plane-like source 21 and transmitted through the subject, and the gamma-rays, which are emitted from RI and prescribed to the subject, are made incident onto the detection surface 47 of the gamma-ray detector 19.

The plane-like source 21 is defined as a source for radiating the gamma-rays based on a substantially equal distribution of radiation. The distribution of radiation approximates the spatially equal distribution of gamma-ray radiation emitted from the plate source. The plate-like source 21 will be specifically explained later.

Just for convenience, a rotating coordinate system is defined that a center of a photographing area, which is sandwiched between the detection surface 47 of the gamma-ray detector 19 and a radiation surface of the plane-like source 21, is an original point, an X axis is parallel to the detection surface 47, a Y axis is parallel to a normal line of the detection surface 47, and a rotate axis is a Z axis.

The rotate mechanism 23 comprises a mechanism and a driving source, which is necessary for the rotation around the subject as maintaining the state that the gamma-ray detector 19 and the plane-like source 21 are opposite to each other to sandwich the subject therebetween.

The slide mechanism 25 comprises a mechanism, which is necessary for sliding the plane-like source 21 to be parallel to the Z axis (body axis), a driving source.

At the time of photographing, the subject mounted on a bed is normally set such that its body axis is substantially consistent with the rotate axis of the rotate mechanism and that at least one section of interest is moved to enter a photographing area.

The scan controller 15 has a rotate controller 27, and a slide controller 29. The rotate controller 27 controls the rotate mechanism 23 such that the gamma-ray detector 19 and the plane-like source 21 rotate around the subject in accordance with a predetermined rule at the time of photographing. Thereby, the stop and rotation of the gamma-ray detector 19 and the plane-like source 21 are intermittently repeated every predetermined angle such as 5° at the time of photographing.

The slide controller 29 comprises a mechanism, which is necessary for sliding the plane-like source 21 to be parallel to the Z axis, and a driving source. Also, the slide controller 29 is structured such that the plane-like source 21 is intermittently or continuously slid at pitch Δ to be described later.

The processor unit 17 comprises a counting processor 31, a reconstructing processor 33, an absorption coefficient calculating processor 35, an absorption correcting processor 37, and a displaying unit 39.

Among the gamma-rays made incident to the gamma-ray detector 19, the counting processor 31 counts the number of the gamma-rays having energy, which is in the range of a predetermined energy window, at each of incident positions and each of angles based on outputs of the gamma-ray detector 19.

The apparatus can be selectively operated in first and second operation modes by the control of the system controller 11.

In the first operation mode, the gamma-rays, which are emitted from the plane-like source 21 and transmitted through the subject, are detected by the gamma-ray detector 19. Then, an absorption coefficient map (A-C-MAP), which is necessary for correcting absorption, is generated based on the number of counts. The absorption coefficient map is a two-dimensional distribution of the section of interest.

In the second operation mode, the gamma-rays, which are emitted from RI and prescribed to the subject, are detected by the gamma-ray detector 19, thereby reconstructing the two-dimensional distribution showing the number of RIs of the section of interest, that is, emission computed tomogram.

In the first operation mode, transmission data is output from the counting processor 31. In the second operation mode, emission data is output from the counting processor 31. Transmission data and emission data, serving as data showing a count number of of the incident gamma-rays of each of the incident positions and that of each of angles, can be obtained by the same counting process.

Transmission data has substantially the same meaning as projection data of the X-ray CT. Transmission data corresponds to a set of the number of counts, which is counted when the gamma-ray detector 19 and the plane-like source 21 rotate around the subject. The number of counts corresponds to an integral of the absorption coefficient of a tissue of the subject on each of the paths of the gamma-rays. For example, a part of 100 gamma-rays emitted from the plane-like source 23 is absorbed in the subject, and the other gamma-rays, e.g., 10 gamma-rays are transmitted through the subject, and detected to be counted. The number of the gamma-rays, which are emitted from a unit area for a unit period of time, is peculiar to RI density of the plane-like source 23. Due to this, the number of counts (number of transmitted gamma-rays) reflects the absorption coefficient on the path of the corresponding gamma-ray.

Emission data corresponds to a set of the number of counts, which is counted when the gamma-ray detector 19 and the plane-like source 21 rotate around the subject. The number of counts corresponds to the number of RIs existing on each of the paths of the gamma-rays.

The first and second operation modes are selected in a time shearing manner by the system controller 11.

The reconstructing processor 33 reconstructs the two-dimensional distribution of the number of transmitted gamma-rays of the section of interest (transmission-computed-tomogram data TCT DATA) based on transmission data. Also, the reconstructing processor 33 reconstructs the two-dimensional distribution of the number of RIs of the section of interest (emission-computed-tomogram data ECT DATA) based on emission data.

Emission-computed-tomogram data wherein no absorption correction is made is defined as original-emission-computed-tomogram data (ORIGINAL ECT DATA) in order to be distinguished from emission-computed-tomogram data (ECT DATA) wherein absorption correction is made.

The absorption coefficient calculating processor 35 calculates the two-dimensional distribution of the absorption coefficient of the section of interest, that is, absorption-coefficient-map (A-C-MAP), based on transmission-computed-tomogram data.

The following will briefly explain the calculation method for absorption coefficient since such a method is well known.

More specifically, absorption coefficient μ is calculated based on the following equation:

$$I_1 = I_0 \times \exp(-\mu \times L)$$

wherein the number of gamma-rays emitted from the unit area, which corresponds to one pixel of the plane-like source 21, for a unit period of time is $I_0$, the number of gamma-rays, which is transmitted through the subject and detected to be counted, is $I_1$, and a length of each path of the gamma-rays is L.

The absorption correcting processor 37 corrects (absorption correction) ORIGINAL ECT DATA based on the absorption-coefficient-map (A-C-MAP), thereby obtaining ECT DATA. ECT DATA is displayed on a displaying unit 39.

The following will explain the plane-like source 21.

Figure 7:
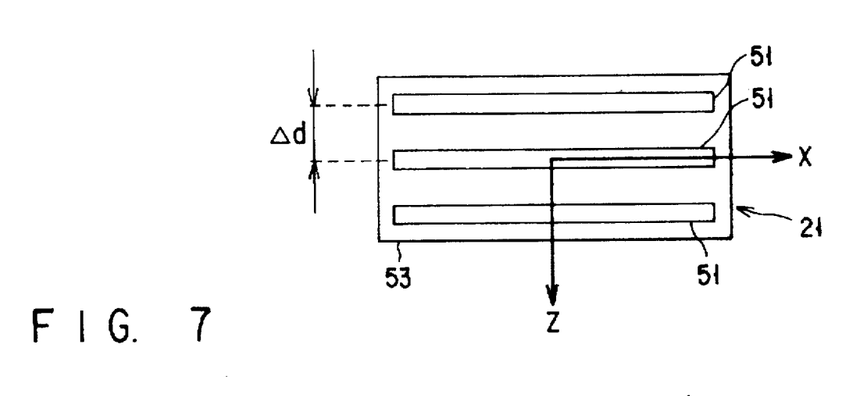
FIG. 7 is a plane view of the plane-like source of FIG. 4.
Figure 8:
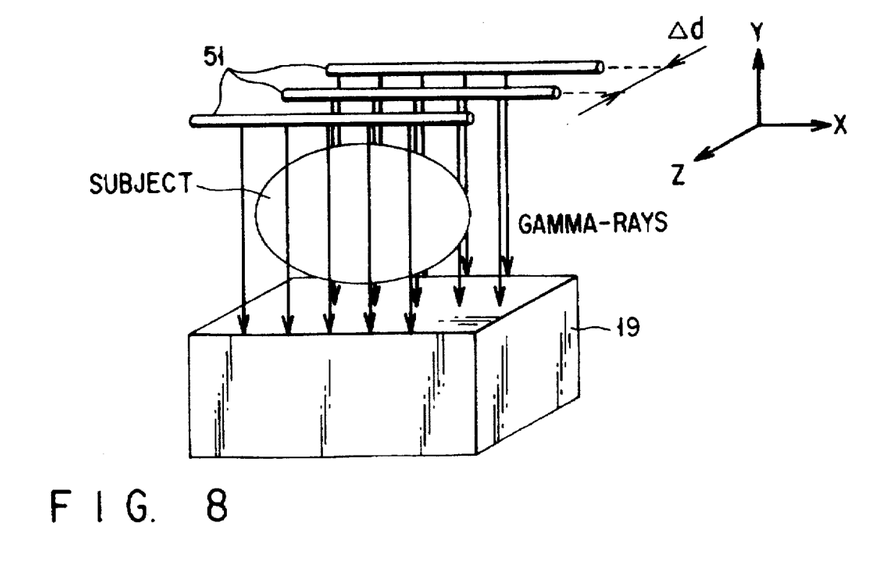
FIG. 8 is a perspective view of the plane-like, source of FIG. 4.

FIG. 7 is a plane view of the plane-like source 21, and FIG. 8 is a perspective view of the plane-like source 21. The plane-like source 21 has a plurality of linear line sources 51, and a flat-shape frame 53 to which the line sources 51 are fixed. Each of the line sources 51 is formed as follows.

More specifically, a rod-shape closed container is filled with RI solution, or RI particles are rod-molded.

Each of the line sources 51 is formed along the X axis where its long axis is perpendicular to the body axis (Z axis) of the subject. The line sources 51 are dispersedly arrayed at a predetermined pitch Δd or n×Δd with respect to the body axis (Z axis) of the subject. In this case, n is a real number.

Figure 9:
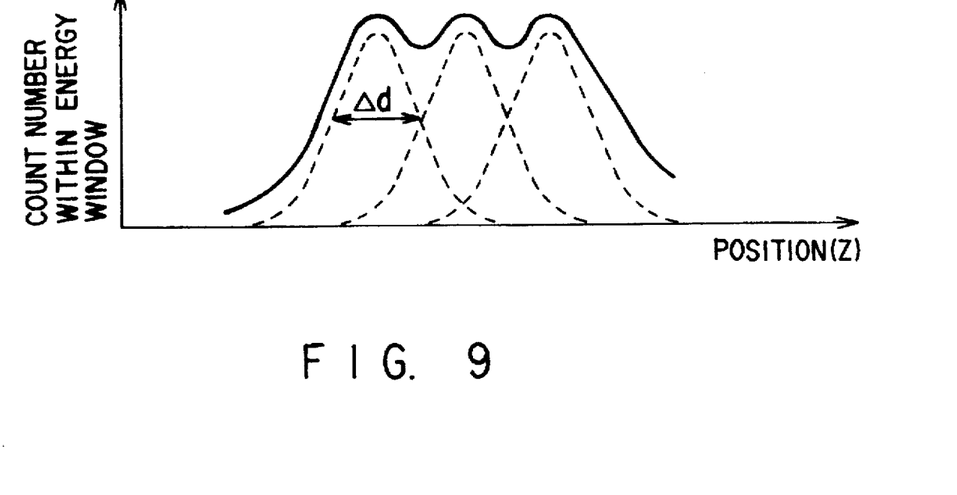
FIG. 9 is a view showing a distribution of radiation of gamma-rays along a body axis.

FIG. 9 shows a radiation distribution on the Z axis measured when a phantom having an equal thickness and absorption rate is used. A dotted line shows a distribution of radiation regarding to gamma-rays radiated from one line source 51, and Δd is set to a half-width or an integral multiple of a half-width corresponding to a peak of the distribution of radiation shown by the dotted line. In other words, the line sources 51 are arrayed at pitch of the half-width of the corresponding distribution of radiation or pitch of an integral multiple of the half-width.

A solid line show a distribution of radiation corresponding to three line sources 51 arrayed at the pitch of the corresponding half-width. As shown by the solid line, the line sources 51 are arrayed at pitch Δd of the corresponding width, so that the concave and convex of the distribution of radiation are relaxed. As a result, a distribution of radiation, which approximates the linear distribution of radiation of the plane source, can be obtained.

This means that a three-dimensional absorption coefficient map can be prepared by lighter plane-like source 21 with the same accuracy as the case in which the plane source having the same size as the plane-like source 21 is used.

If the line sources 51 are arrayed at pitch of n×66 d, the plane-like source 21 is intermittently slid at pitch Δd, so that a large range of data can be collected for a short period of time. This means that the absorption coefficient map, which has the same accuracy as an extremely large plane source covering the corresponding large range, can be prepared by the lighter plane-like source 21.

Moreover, the detection of the transmitted gamma-rays is continued as the plane-like source 21 is being slid for a distance of n×Δd at a fixed speed. This means that the absorption coefficient map, which has the same accuracy as the extremely large plane source covering the range where the plane-like source 21 slides, can be prepared by the lighter plane-like source 21.

As mentioned above, according to the embodiment of the present invention, the line sources 51 are provided in the direction, which is perpendicular to the body axis of the subject. Thereby, the high accurate absorption coefficient map of the section of the subject can be obtained. Therefore, there can be realized the absorption correction of the section of the subject with high accuracy.

Also, according to the embodiment of the present invention, the plurality of the line sources are arrayed to have the half-width Δd of the distribution of radiation or the pitch of n×Δd. Due to this, the absorption coefficient map having the accuracy, which is equal to the heavy plane-like source or the same as the heavy plane-like source, can be prepared by the light plane-like source.

Figure 10:
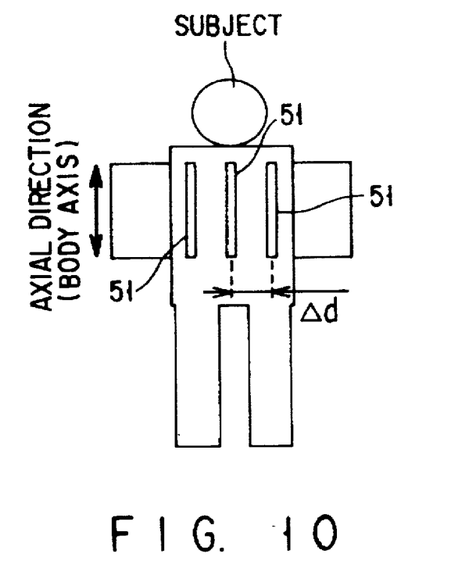
FIG. 10 is a view showing a first modification of the plane-like source of FIG. 4.
Figure 11:
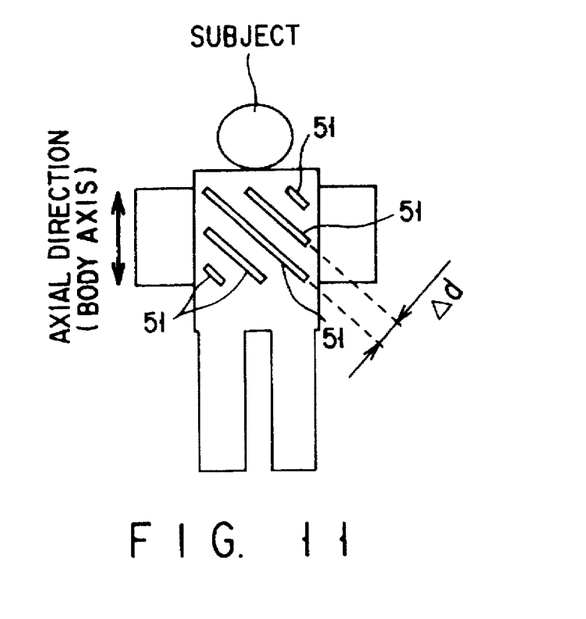
FIG. 11 is a view showing a second modification of the plane-like source of FIG. 4.

The plane-like source may be modified as shown in FIGS. 10 and 11. In a first modification of FIG. 10, the line sources 51 are formed such that their long axes are be parallel to the body axis (Z axis). In a second modification of FIG. 11, the line sources 51 are formed such that their long axes obliquely cross the body axis (Z axis). Even in these modifications, the line sources 51 are arrayed at pitch Δd.

Figure 12:
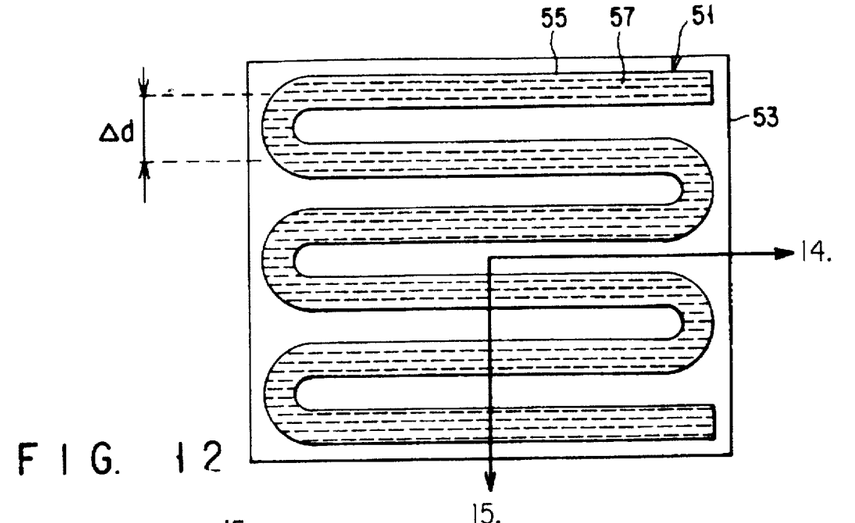
FIG. 12 is a view showing a third modification of the plane-like source of FIG. 4.
Figure 13:
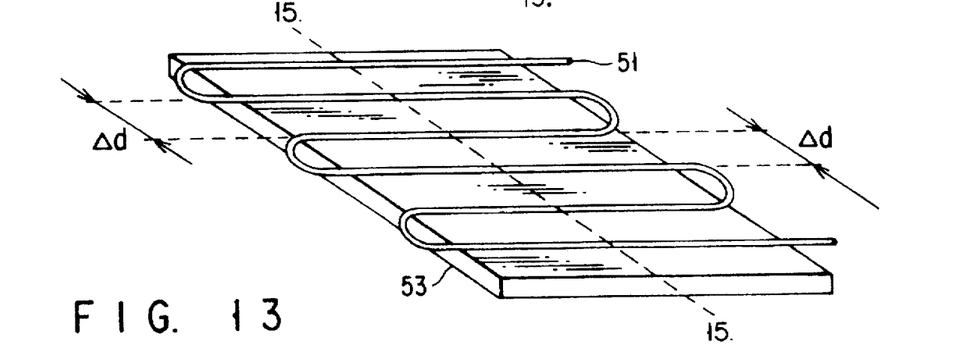
FIG. 13 is a perspective view of the plane-like source of the third modification.
Figure 14:
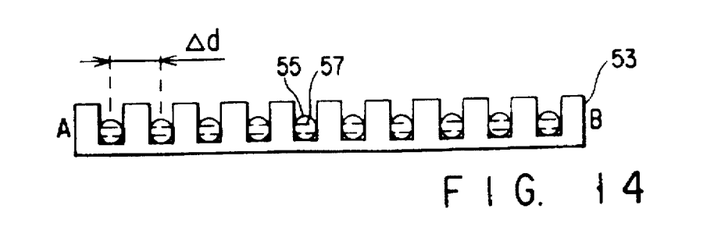
FIG. 14 is a cross sectional view taken along a line A–B of FIG. 13.

Moreover, the plane-like source 21 may be modified as in a third modification shown in a plane view of FIG. 12, a perspective view of FIG. 13, and a cross sectional view of FIG. 14. In the third modification, for example, the line source 51, which is formed of a flexible polytetrafluorethylene-made tube 55 filled with RI solution 57, is bent at a plurality of portions. In other words, the line source 51 is provided in a plane form, and has a plurality of straight line portions and a plurality of bent portions. The plurality of straight line portions are arrayed such that their portions are perpendicular or parallel to the body axis of the subject. Also, the straight line are dispersedly arrayed to be parallel to each other at pitch of Δd or n×Δd. Moreover, if the line source 51 is entirely flat formed, the line source 51 may be formed to be spiral or to have the other shape.

Figure 15:
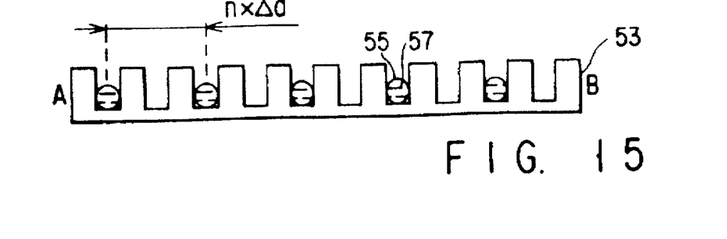
FIG. 15 is a cross sectional view taken along a line A–B of FIG. 13.

An inner diameter of the tube 55 is preferably set to about 1 to 2 mm in order to reduce scattering lines. As shown in FIG. 15, in the third modification, the pitch of each of the straight line portions can be changed to pitch of n×Δd. In this case, for example, a child subject is generally smaller than an adult subject, and the gamma-rays can be easily transmitted through the child subject. Due to this, the pitch can be widened in the case of the child subject.

Figure 16:
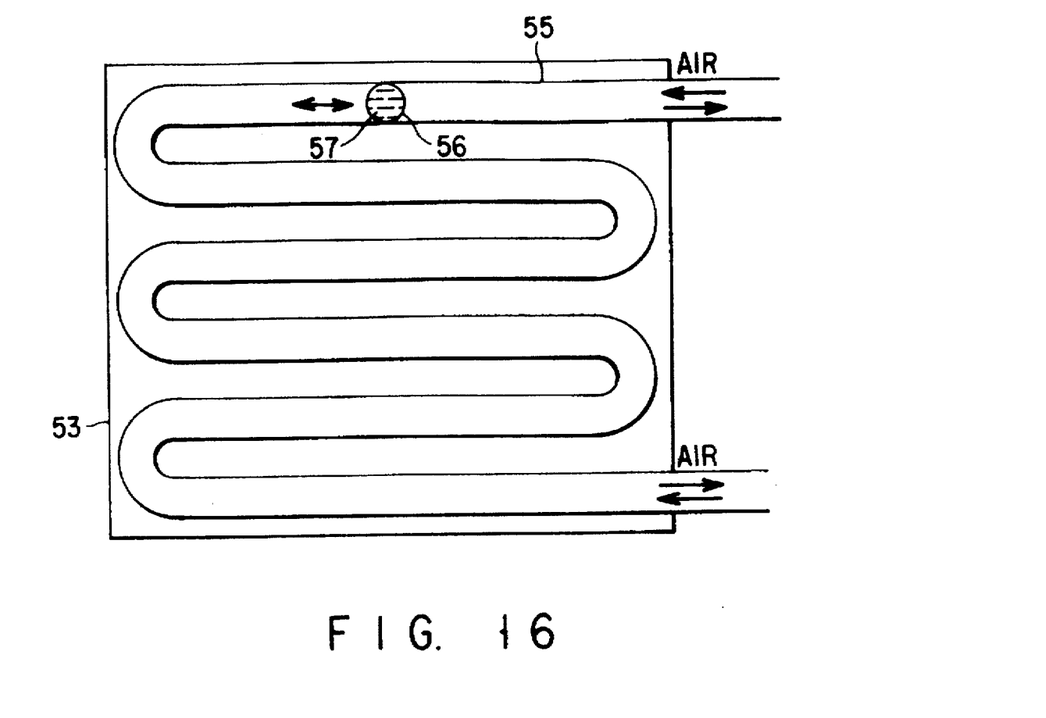
FIG. 16 is a view showing a fourth modification of the plane-like source of FIG. 4.

The plane-like source 21 may be modified as shown in the plane view of FIG. 16 (fourth modification). In the fourth modification, similar to the third modification, the flexible polytetrafluorethylene-made tube 55 is provided in a plane form. Then, a polytetrafluorethylene-made spherical case 56, which is filled with RI solution 57, is inserted into the flexible polytetrafluorethylene-made tube 55 to be circulatable. The case 56 is equivalent to the so-called point-source. The tube 55 has a plurality of straight line portions and a plurality of bent portions. The plurality of straight line portions are arrayed such that their portions are perpendicular or parallel to the body axis of the subject. Also, the straight line are dispersedly arrayed to be parallel to each other at pitch of Δd or n×Δd.

Figure 17:
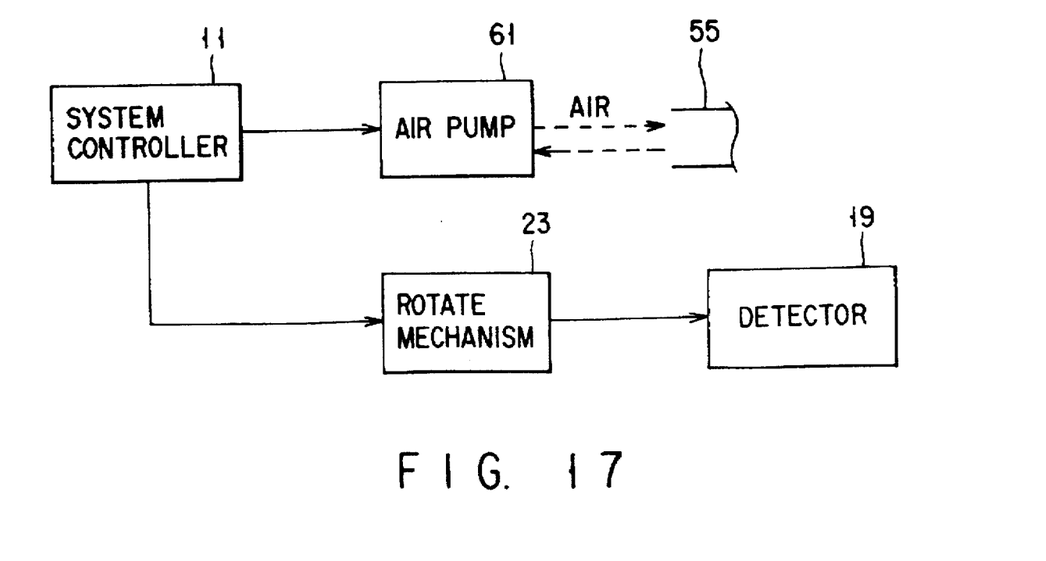
FIG. 17 is a block diagram of a drive system of the fourth embodiment.

Air is supplied to the tube 55 from a pump 61 of FIG. 17 in a forward direction or an opposite direction. Thereby, the case 56 reciprocates in the tube 55. The pump 61 is controlled by the system controller 11 to be synchronized with the rotation of the detector 19. Thereby, the case 56 is circulated in the tube 55 from the end to the end or a designated position to a designated position at a fixed speed during the stop of the detector. In place of air, liquid such as water or oil may be supplied to the tube 55 to circulate the case 56 in the tube 55.

Figure 18:
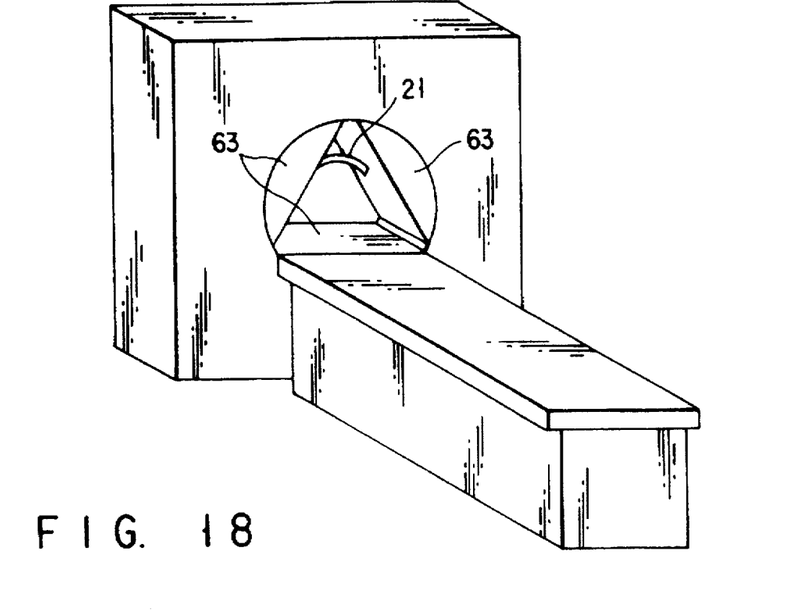
FIG. 18 is an outline view of an apparatus dedicated to SPECT (signal photon emission computed tomography) of a three-detector type.
Figure 19:
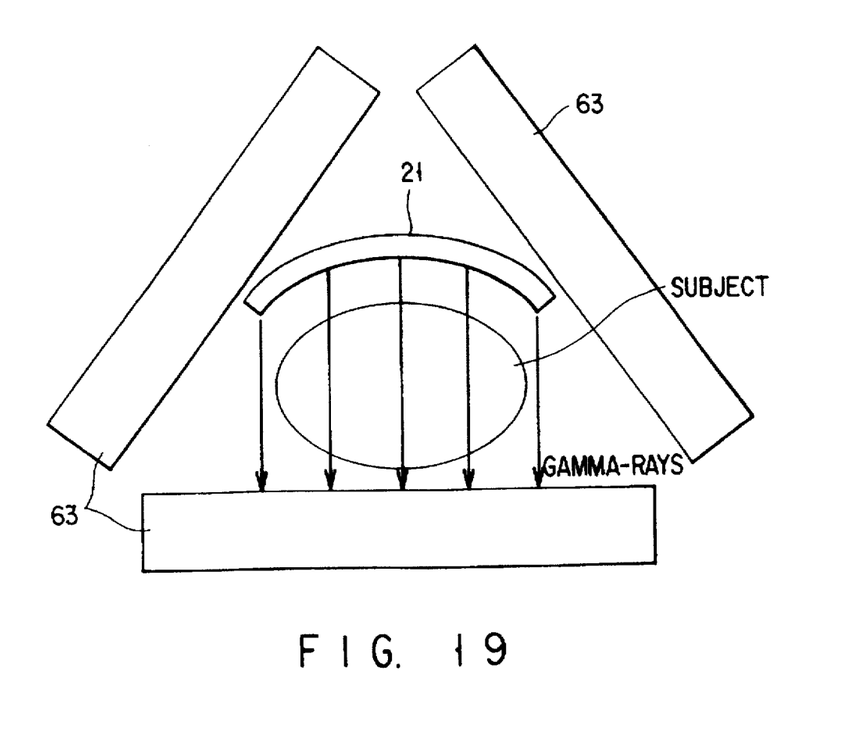
FIG. 19 is a view showing an application of the plane-like source to SPECT of the three-detector type.

As shown in FIGS. 18 and 19, the plane-like source 21 is bent, thereby the present invention may be applied to an apparatus dedicated to SPECT (signal photon emission computed tomography) of a three-detector type.

Also, in a case of an opposite two-detector typed apparatus, the plane-like source 21 is provided at a front of one detector. In this case, in order to move the detector along the surface of the subject, a support member for supporting a distance sensor is provided at both ends of the front of the detector. The support member is attached to a position, which is several centimeters away from the detection surface. The rails 44 may be formed on the support member of the sensor.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. In a nuclear medicine diagnostic apparatus, the improvement comprising a source of gamma-rays for an absorption correction, wherein said source has a plurality of line sources, each line source producing a radiation distribution having a peak and defining a half-width distance at which the radiation from said line source is attenuated by one-half said plurality of line sources arrayed at a pitch equal to the half-width distance.

2. The apparatus according to claim 1, wherein said line sources are arrayed to be parallel to each other.

3. The apparatus according to claim 1, wherein said line sources are provided in a direction substantially perpendicular to a body axis of a subject.

4. The apparatus according to claim 1, wherein said line sources are provided to be inclined to a body axis of a subject.

5. The apparatus according to claim 1, wherein said line sources are provided to be parallel to a body axis of a subject.

6. The apparatus according to claim 1, wherein said line sources are arrayed in a common plane.

7. The apparatus according to claim 1, comprising means for sliding said source of gamma-rays along an array direction perpendicular to a longitudinal axis of said line sources.

8. The apparatus according to claim 7, wherein said line sources are arrayed to be parallel to each other, and said source of gamma-rays is slid at a fixed speed by said sliding means.

9. The apparatus according to claim 7, wherein said line sources are arrayed to be parallel to each other at a pitch of two or more integral multiples of the half-width distance, further comprising sliding means for intermittently sliding said source of gamma-rays in increments equal to said pitch.

10. In a nuclear medicine diagnostic apparatus, the improvement comprising a source of gamma-rays for an absorption correction, wherein said source has a plurality of line sources, each line source producing a radiation distribution having a peak and defining a half-width distance at which the radiation from said line source is attenuated by one-half, wherein said line sources are arrayed at a pitch of an integral multiple of the half-width distance.

11. In a nuclear medicine diagnostic apparatus including a source of gamma-rays for an absorption correction, the improvement comprising said source comprising a line source provided in a plane form and having a plurality of straight line portions and a plurality of bent portions, said straight line portions arrayed parallel to each other at intervals.

12. The apparatus according to claim 11, wherein said straight line portions extend in a direction substantially perpendicular to a body axis of a subject.

13. The apparatus according to claim 11, wherein said straight line portions are provided to be inclined to a body axis of a subject.

14. The apparatus according to claim 11, wherein said straight line portions are provided to be parallel to a body axis of a subject.

15. The apparatus according to claim 11, wherein said straight line portions are arrayed at a fixed pitch.

16. The apparatus according to claim 11, wherein each straight line portion produces a radiation distribution having a peak and defining a half-width distance at which the radiation from said line source is attenuated by one-half, and said straight line portions are arrayed at a pitch equal to the half-width distance.

17. The apparatus according to claim 11, wherein each straight line portion produces a radiation distribution having a peak and defining a half-width distance at Which the radiation from said line source is attenuated by one-half, and said straight line portions are arrayed at a pitch equal to an integral multiple of the half-width distance.

18. The apparatus according to claim 11, comprising means for sliding said source of jamma-rays along an array direction perpendicular to a longitudinal axis of said straight line portions.

19. The apparatus according to claim 18, wherein said source of gamma-rays is slid at a fixed speed by said sliding means.

20. The apparatus according to claim 11, wherein each straight line portion produces a radiation distribution having a peak and defining a half-width distance at which the radiation from said line source is attenuated by one-half, and said straight line portions are arrayed to be parallel to each other at a pitch of two or more integral multiples of the half-width distance.

21. The apparatus according to claim 20, comprising means for sliding said source of jamma-rays along an array direction perpendicular to a longitudinal axis of said straight line portions.

22. The apparatus according to claim 20, wherein said source of gamma-rays is intermittently slid in increments equal to said pitch by said sliding means.

23. The apparatus according to claim 11, wherein said line source defines a circulation path provided in said plane form and includes a point-source circulating with said circulation path.

24. The apparatus according to claim 23, wherein said apparatus has means for driving the circulation of said point-source.

* * * * *